United States Patent [19]

Antonini

[11] 4,029,771
[45] June 14, 1977

[54] COMPOSITION FOR THE TREATMENT OF BACTERIAL-INTESTINAL INFECTIONS

[76] Inventor: Eraldo Antonini, Via Di Parione 37, Rome, Italy

[22] Filed: Apr. 21, 1976

[21] Appl. No.: 678,752

[30] Foreign Application Priority Data

Apr. 23, 1975 Italy .................................. 22652/75

[52] U.S. Cl. .............................................. 424/177
[51] Int. Cl.² ....................................... A61K 37/02
[58] Field of Search ............................. 424/177, 95

[56] References Cited
OTHER PUBLICATIONS

Chemical Abstracts, 46:11325 g (1952).

Primary Examiner—Jerome D. Goldberg

[57] ABSTRACT

A composition for the treatment of bacterial-intestinal infections, especially in infants, containing as an essential ingredient thereof, an effective amount of conalbumen.

4 Claims, 1 Drawing Figure

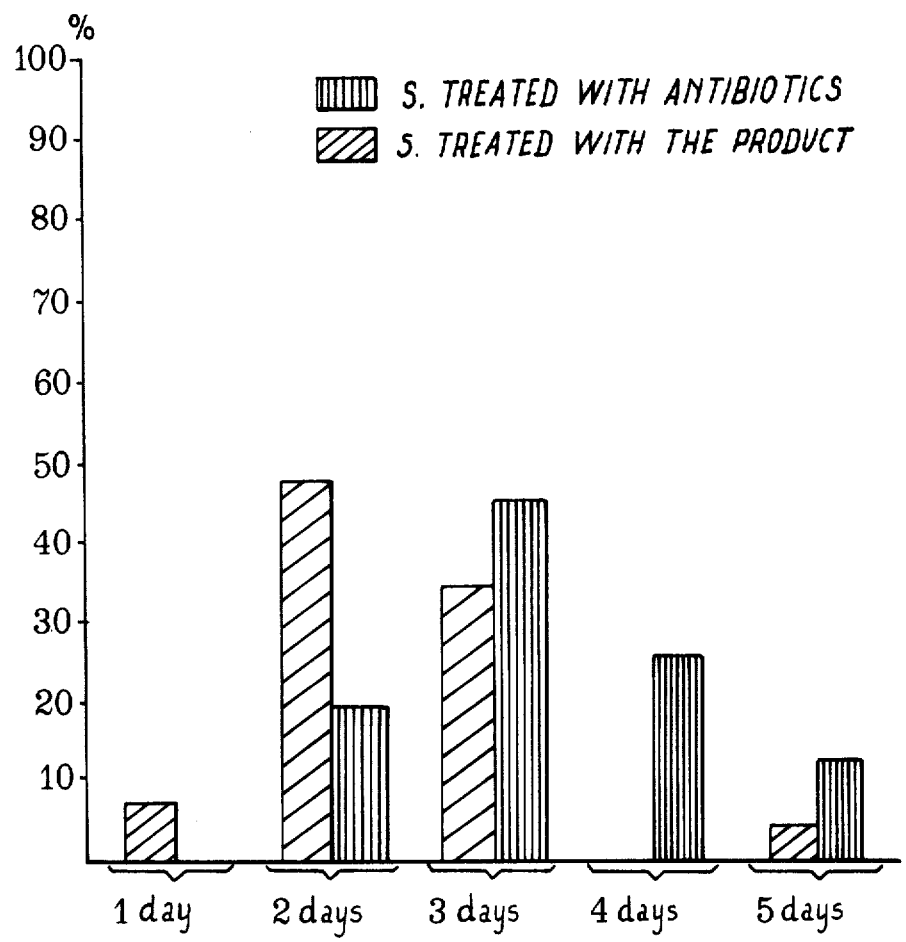
TABLE 1

COMPOSITION FOR THE TREATMENT OF BACTERIAL-INTESTINAL INFECTIONS

The present invention relates to a bacteriostatic agent having a high degree of therapeutic efficacy against intestinal bacterial infections.

It is known that some biological liquids, such as blood, milk, egg white and others, contain proteinaceous substances which have the ability to strongly bind iron and other metals. Said proteinaceous substances are known as transferrins, one of the most representative being conalbumen.

In a copending application filed by the same applicant there is described a method for the extraction of transferrins, particularly of conalbumen, in a pure state from the abovementioned biological liquids. In particular, said method permits the preparation of large quantities of said proteins, particularly of ovotransferrin or conalbumen, from egg white, in a manner which is simple and rapid, and consequently economical.

It has now been unexpectedly found that the transferrines, particularly conalbumen, especially if obtained by the method described in the mentioned patent application are useful therapeutic agents against intestinal bacterial infections, particularly in infants.

The transferrin is used in a liophylized form and administered orally, for example dissolved in a suitable liquid vehicle, such as water.

The product can be kept for indefinite periods in vials containing 100 mg. or more of the product in a liophylized form.

The product has been tried in the treatment of experimental infections in laboratory animals injected with germs which are pathogenic to man for the therapy of pathological states characterized by bacterial enteritis, and has shown a surprising efficacy. It has also been shown that the administration of the product to experimental animals in therapeutically active doses does not result in toxic manifestation or in significant side effects.

A method for obtaining conalbumen of extreme purity is the following:

There is first prepared a complex $Fe^{+++}$ carboxymethylcellulose.

To prepare said complex, 1.5 Kg. of carboxymethylcellulose (type CM - 52 Whatman, microgranular, preswollen) are dispersed into distilled water, treated with 4-5 volumes (approximately 10:1) of an aqueous solution of $FeCl_3$ (0.5 M) and stirred for 4 hours. The thus formed Fe-CMC complex is then filtered on a Buchner funnel and the residue is repeatedly washed with distilled water until there is no further trace of $Fe^{+++}$ ions in the filtrate.

The resinous product is then transferred into a suitable vessel and is treated with 4–5 volumes of 1M $NH_4OH$ (about 8:1) stirring for 4 hours. It is then filtered on a Buchner funnel and washed with distilled water until the filtrate has a pH between 7 and 8. At this point the resinous product is transferred into a suitable vessel and stirred for at least 30 minutes with 3–4 volumes of acetate buffer (0.1 M, pH=5), if necessary adjusting the pH to a value of 5.

10 Kg. of egg albumen (integral egg white) are deionized by means of mixed amionic-cationic ion exchange resin (batch mixing).

The thus deionized albumen is gravity filtered through cheese-cloth; the pH of the filtrate is adjusted to 5 and the resulting product is again filtered through fluted filter paper. The pH of the resulting filtrate, which is completely clear, is recontrolled (it should have a value of pH 5), readjusted if necessary and then there is added thereto 1/10 of its volume of acetate buffer (0.1 M, pH = 5) and the resulting solution stirred for few minutes.

The solution thus obtained is then passed through the Fe-CMD resin, prepared as hereinbefore described, placed upon a suitable Buchner funnel provided with a suitable filter paper. The progressive adsorbment of the conalbumen can be visually followed by noting the formation of a light-brown layer on the original dark-brown layer of the Fe-CMC. When all the liquid has passed through the layer, said layer is washed with acetate buffer (0.1 M, pH=5) until the filtrate shows no further trace of proteins; then the conalbumen is eluted using as an eluent acetate buffer (0.1M, pH=5.5) containing sodium citrate $2 \times 10^{-3}M$ (0.2 ml. of sodium citrate 1M in 100 ml of acetate buffer 0.1 M, pH of 5.5).

The conalbumen solution thus obtained is deironized by known means, such as by bringing the pH to 4.7 with solid citric acid and then treating the resulting mixture repeatedly by batch mixing with strong cationic resins, such as those commercially known under the trademarks of Dowex IX-2 (Cl) or IRA-400 (Cl), for individual periods of 25–30 minutes, and each time filtering and controlling the pH to assure that it remains at a value of 4.7. The deironized liquid, brought to a pH of 6.5 with concentrated NaOH is dialyzed with cold distilled water (3°–4° C) with frequent changes of the dialyzing liquid for at least 48 hours. The dialyzate, gravity filtered through paper, is then liophylized. The product obtained is then controlled spectrophotometrically (278 nm in the UV spectrum in 0.02 M HCl and at 470 and 400 nm in the visible spectrum as Fe-conalbumin) and electrophoretically and results as consisting essentially of pure conalbumin.

The yield is about 10 grams of conalbumen for each Kg. of albumen.

The liophylized conalbumen maintains its properties unchanged for at least 6 months if kept at ambient or lower temperature. The present invention concerns the use of a compound, the essential ingredient of which is conalbumin, for treating acute gastroentheropathy in children. The invention involves both the compound for the treatment of acute gastroentheropathy as well as the method of administering it. The following tests are illustrative of the toxicity and efficacy of the invention. The toxicity tests were performed on rats and mice, while the efficacy tests exemplify the favorable results obtained by carrying out the method of the present invention on thirty-two specific children being treated with a specific amount of the composition according to the invention for the treatment of a specific bacterial infection, namely acute gastroentheropathy.

The toxicity and the activity of the present compound were determined as follows:

TOXICITY a. Toxicity on single administration.

The experiment was conducted on rats and mice (male and female) by oral and intraperitoneal administration of conalbumen dissolved in double-distilled sterile water. The animals were kept under control for 7 days following the administration.

The results obtained in the texts are summarized in the following Table 1.

TABLE 1

Acute toxicity of the product after a single administration to the male and female rat (Sprague-Dawley).

| Dosages mg/kg | Method of administration | Sex and weight (g) | No. of rats per dose | Mortality after 7 days | $LD_{50}$ mg/kg |
|---|---|---|---|---|---|
| 1000 | oral | M.100–130 | 10 | 0/10 | >1000 |
| 1000 | oral | F. 90–105 | 10 | 0/10 | >1000 |
| 1000 | i.p. | M.100–120 | 10 | 0/10 | >1000 |
| 1000 | i.p. | F.100–110 | 10 | 0/10 | >1000 |

EFFICACY

The tests were conducted on a group of 32 children (14 males, 18 females) of an age group comprised between 2 months and 2 years, affected by acute initial gastroenteropathy.

The test group comprised forms of substantial gravity (15.6% of the total cases), forms of intermediate gravity (43.7%), and finally forms of least gravity (40.6%), determined by known clinical diagnostic methods.

In all cases, in addition to the oral or parental rehydration (in 21.8% of the cases there was actually performed a parental rehydration with glucosaline and polyelectric solutions) and to the usual dietetic treatment, there was performed symptomatic therapy with anticholinergic agents.

The product was administered orally to all the test subjects at a dosage of 300 mg. per day, divided into three equal doses.

The duration of the therapy varied from a minimum of 5 days to a maximum of 10 days.

It was thought opportune, on a clinical plane, to evaluate the test results according to the following parameters:

1. average time of normalization of the abdomen.
2. number and percentage of the cases with regularization of the abdomen within the first 48 hours (see Table II and figure 1).
3. average duration of the time of therapy.

There was further compared the test subjects with a group of subjects of similar age and equally affected by acute initial gastroenteropathy which had received, in addition to the usual symptomatic and dietetic therapy, a chemiantibiotic treatment.

It is important to note that this second group presented a clinical physionomy similar to that of the test group (and therefore with a percentage division equal between forms of different gravity) and further belonging chronologically to the same epidemiological period.

The comparison between the two groups reported on Table II and in the drawing permits the reaching of the following conclusions:

1. The average time of normalization of the abdomen is slightly lower in the subjects treated with the present product than in those treated with chemiantibiotics.
2. The number of cases and the percentage of normalization of the abdomen within the first 48 hours is higher in the subjects treated with the present product.
3. The drawing, which indicates the percentage distribution in the time of normalization of the abdomen in the two groups in question, shows that the cases treated with the present product are distributed essentially between the second and third day (with a peak in the second day), whereas the control group presents the highest percentages in the third and fourth day (with a peak in the third day).

It therefore follows that the clinical results are very favorable in the group treated with the present product and definitely better with respect to the group treated with chemiantibiotics.

I claim:

1. A method of treating acute bacterial gastroentheropathy in children, comprising orally administering to each infected child conalbumen in a dosage of about 300 mg per day.
2. The method as claimed in claim 1 wherein said dosage of 300 mg per day is administered in three equal 100 mg dosages.

|  | Total Case | Average time of normalization of the abdomen | No. of cases with normalization within 48 hours | Percentage normalization within 48 hours | Average time of Therapy |
|---|---|---|---|---|---|
| Subjects treated with the present product | 32 | 2.56 (*) | 17 | 53.1 | 6.1 days |
| Subjects treated with chemicoantibiotics | 32 | 3.31 (*) | 6 | 18.7 | 6.6 days |

(*) p <0.40

3. The method as claimed in claim 1, wherein said dosage of 300 mg per day is administered for a period of 5 to 10 days.

4. The method as claimed in claim 1 wherein the conalbumen is administered in the form of a composition.

* * * * *